US009262866B2

(12) United States Patent
Tsao et al.

(10) Patent No.: US 9,262,866 B2
(45) Date of Patent: Feb. 16, 2016

(54) AUGMENTED REALITY METHODS AND SYSTEMS INCLUDING OPTICAL MERGING OF A PLURALITY OF COMPONENT OPTICAL IMAGES

(71) Applicant: Vantage Surgical Systems, Inc., Los Angeles, CA (US)

(72) Inventors: Tsu-Chin Tsao, Manhattan Beach, CA (US); Jason Wilson, Santa Ana, CA (US)

( * ) Notice: Subject to any disclaimer, the term of this patent is extended or adjusted under 35 U.S.C. 154(b) by 0 days.

(21) Appl. No.: 14/456,901

(22) Filed: Aug. 11, 2014

(65) Prior Publication Data
US 2014/0347395 A1   Nov. 27, 2014

Related U.S. Application Data

(62) Division of application No. 13/164,671, filed on Jun. 20, 2011, now Pat. No. 8,836,723.

(60) Provisional application No. 61/356,150, filed on Jun. 18, 2010.

(51) Int. Cl.
| G06F 3/038 | (2013.01) |
| G09G 5/00 | (2006.01) |
| G06T 19/00 | (2011.01) |
| A61B 19/00 | (2006.01) |
| G02B 26/00 | (2006.01) |
| G06T 11/60 | (2006.01) |
| G02B 27/01 | (2006.01) |
| G02B 27/10 | (2006.01) |

(52) U.S. Cl.
CPC ............. *G06T 19/006* (2013.01); *A61B 19/00* (2013.01); *A61B 19/5225* (2013.01); *G02B 26/00* (2013.01); *G02B 27/01* (2013.01); *G06T 11/60* (2013.01); *A61B 2019/5291* (2013.01); *G02B 27/1066* (2013.01); *G02B 2027/014* (2013.01); *G02B 2027/0138* (2013.01)

(58) Field of Classification Search
CPC ... G01J 3/2823; H04N 9/3105; H04N 9/3197; G02B 27/1066; G02B 2027/0138; G02B 2027/014
USPC ...................... 345/204, 629–633; 353/30, 34; 356/456–458
See application file for complete search history.

(56) References Cited

U.S. PATENT DOCUMENTS 6,997,560 B2 *  2/2006  Shade ............................. 353/31

* cited by examiner

*Primary Examiner* — Gustavo Polo
(74) *Attorney, Agent, or Firm* — Siber Law, LLP; Victor Siber; Andres F. Arrubia

(57) ABSTRACT

The present disclosure provides augmented reality methods and systems where two or more component optical images are optically overlaid via one or more beam splitters to form composite optical images. In some embodiments a second component optical image is an electronic optical image (an image from an electronically controlled emission source) while the first component optical image is one of a physical optical image (an image of a physical object from which diffuse reflection occurs), an electronic optical image, an emission optical image (an image from a non-electronic source that emits radiation), or a hybrid optical image (composed of at least two of a physical optical image, and electronic optical image, or an emission optical image). In some embodiments the first and second component optical images are used to provide feedback concerning the quality of the overlaying and appropriate correction factors to improve the overlay quality.

9 Claims, 4 Drawing Sheets

AUGMENTED REALITY METHODS AND SYSTEMS INCLUDING OPTICAL MERGING OF A PLURALITY OF COMPONENT OPTICAL IMAGES

RELATED APPLICATIONS

This Application is a divisional application of U.S. Non-Provisional application Ser. No. 13/164,671 which claims the benefit of U.S. Provisional Patent Application No. 61/356,150 filed Jun. 18, 2010. The referenced applications are incorporated herein by reference as if set forth in full herein.

FIELD OF THE INVENTION

The present invention relates generally to the field of imaging, more particularly to the field of augmented reality where two or more images are overlaid and viewed together by an observer, and even more particularly to such systems and methods wherein the merging of at least two component optical images into a composite optical image which are to be viewed together occurs optically. In the various embodiments a second component optical image is an electronic optical image (an image from an electronically controlled emission source) while the first component optical image is one of a physical optical image (an image of a physical object from which diffuse reflection occurs), an electronic optical image, an emission optical image (an image from a non-electronic source that emits radiation), or a hybrid optical image (which composed of at least two of a physical optical image, and electronic optical image, or an emission optical image).

BACKGROUND OF THE INVENTION

Augmented reality (AR) is a term that is applied to composite optical images and methods and systems for producing those composite optical images wherein the composite optical images are typically composed of component optical images, one of which is typically an image of a physical or real object or scene while another component optical image is computer or electronically created, placed, modified, or manipulated to provide an enhanced or alternative understanding of the physical object or scene.

A need exists in AR methods and systems for forming composite optical images using optical merging of component optical images with improvements in overlaying of the optical component optical images.

SUMMARY OF THE INVENTION

It is an object of some embodiments of the invention to provide an improved AR system and methods for use in medical applications (e.g. tissue and tool viewing during surgery, performance of diagnostic procedures, interpretation of the results of diagnostic procedures, and the like) in manufacturing applications (e.g. product design evaluation and verification, inspection during component manufacturing, component alignment during assembly, inspection after assembly, and the like) and/or in research, applications (e.g. data gathering and presentation, and the like).

It is an object of some embodiments of the invention to provide improved AR systems and methods that provide improved overlaying (i.e. merging) of component optical images when producing a composite optical image.

It is an object of some embodiments of the invention to provide improved AR systems and methods that use optical overlaying for viewing merged component optical images (i.e. composite optical images) of first and second component optical images wherein the second component optical image is an electronic optical image and the first component optical image is one of a physical optical image, an electronic optical image, an emission optical image, or a hybrid optical image wherein electronic capture of updated first images are used in determining updated positioning and orientation information for overlaying the second component optical images with the first component optical images.

It is an object of some embodiment of the invention to provide improved AR systems and methods that use optical overlaying for viewing a plurality of component optical images along with electronic capture of a plurality of component optical images to provide feedback and ability to progressively adjust and minimize overlay errors.

Other objects and advantages of various embodiments of the invention will be apparent to those of skill in the art upon review of the teachings herein. The various embodiments of the invention, set forth explicitly herein or otherwise ascertained from the teachings herein, may address one or more of the above objects alone or in combination, or alternatively may address some other object ascertained from the teachings herein. It is not necessarily intended that all objects be addressed by any single aspect of the invention even though that may be the case with regard to some aspects.

Various terms as used herein may have meanings that are narrowed, enhanced, or simply different from their normal meanings and such terms are explicitly or inherently defined herein, e.g. in the detailed description section to follow.

A first aspect of the invention provides a method for providing composite optical images to an eye or eyes of an observer wherein the composite optical images include first component optical images of an object or source along with second component optical images that are to be displayed in relationship to the first component optical images, the method includes: (a) directing first component optical images along a first optical path to a first beam splitter; (b) directing the first component optical images along second and third optical paths from the first beam splitter to the eye or eyes of the observer and to a first image capture device, respectively; (c) producing first electronic data corresponding to the first component optical images captured by the first image capture device and using said first electronic data in combination with other data to provide second electronic data; (d) providing said second electronic data to an electronic image display device to provide second component optical images which are directed along, a fourth optical path onto a second beam splitter; (e) directing the second component optical images along at least a fifth optical path that extends from the second beam splitter to the eye or eyes of the observer wherein the fifth optical path and second optical path at least partially overlap.

Numerous variations of the first aspect of the invention exist and include, for example: (1) the second beam splitter being the same as the first beam splitter and the second and fifth optical paths being the same optical path; (2) a sixth optical path, extending from the second beam splitter to a second optical image capture device and wherein captured second component optical image information provides at least a portion of the other data and is analyzed in combination with the first electronic data to produce said second electronic data, wherein the second image capture device is the same as the first image capture device; (3) a sixth optical path extending from the second beam splitter to a second optical image capture device and wherein captured second component optical image information provides at least a portion of the other data and is analyzed in combination with the first electronic data to produce said second electronic data, wherein the second image capture device is different from the first image capture device; (4) the first component optical images include optical images selected from the group consisting of (a) physical optical images, (b) electronic optical images, (c) emission optical images, and (4) hybrid optical images; (5) the second beam splitter is different from the first beam splitter; (6) the second beam splitter is different from the first beam splitter and a third beam splitter is provided that is different from both the first and second beam splitters and which is located along the fourth optical path which splits the fourth optical path into one branch that continues to the second beam splitter and one branch that directs the second component optical image onto a second image capture device which in turn provides at least portion of the other data and is analyzed in combination with the first electronic data to produce said second electronic data; (7) the first component optical images include physical optical images and wherein the method additionally includes directing light from a light source onto an object located at the beginning of the first optical path that gives rise to the physical optical images; (8) the first component optical images include physical optical images and wherein the method additionally includes directing light from a light source onto an object located at the beginning of the first optical path that gives rise to the physical optical images, and wherein the light form the light source includes light selected from the group consisting of (a) visible light, (b) UV light, and (c) IR light; (9) the first component optical images include physical optical images and wherein the method additionally includes directing light from a light source onto an object located at the beginning of the first optical path that gives rise to the physical optical images; and one or more optical components are provided between the light source and the object wherein at least one of the one or more optical components is selected from the group consisting of (a) a lens, (b) a mirror, (c) a mechanical or electronic shutter, (d) a prism, (e) a diffraction grating, and (f) a filter; (10) providing one or more optical components located along one or more of the first-fifth optical paths wherein the one or more optical components includes at least one component selected from the group consisting of: (1) a lens, (2) a mirror, (3) a shutter, (4) a prism, (5) a diffraction grating, and (6) a filter; (11) the first and second beam splitters are the same beam splitter and the images reaching the beam splitter via the first and fourth optical paths are provided in time modulated forms such that images reaching the image capture device along the third optical path at selected times are the images carried along the first optical path but not the fourth optical path while at other times the images reaching the image capture device are the images carried along the fourth optical path but not the first optical path; (12) the images represented by the data provided along the second electronic path and displayed by the electronic image display device do not include images provided along the first optical path; (13) the using of the first electronic data includes determining positioning information that places the second component optical images and the first component optical images within a desired tolerance by calculating a display position for the second component optical images based, least in part, on captured positions of the first component optical images; (14) the using of the first electronic data includes determining positioning information that places the second component optical images and the first component optical images within a desired tolerance by calculating a display position for the second component optical images based, least in part, on captured positions of the first component optical images and on spatial comparisons of prior captured first component optical images and prior captured second component optical images; (15) adjusting an optical path by adjusting at least one component of the of system, wherein the component is selected from the group consisting of (a) at least one beam splitter, (b) the display device, (c) at least one image capture device, (d) a positioning of the object, (e) an image focusing component located along one of the optical paths, (f) a filter located along one of the optical paths, (9) a shutter located along one of the optical paths, (h) an aperture located along one of the optical paths, and (i) a mirror located along one of the optical paths; (16) adjusting an optical path by adjusting at least one component of the of system (a) manually during operation, (b) manually during calibration, (c) partially automatically during operation, (d) partially automatically during calibration, (e) automatically during operation, and/or (f) automatically during calibration; (17) automatically adjusting an optical path by adjusting at least one component of the of system using, at least in part, feedback provided by second component images captured by a second image capture device; (18) the using includes processing the first electronic data using a programmed computer that is also programmed to control one or more system components and wherein at least one of the one more system components are selected from: (a) an electronic shutter located along one of the optical paths, (b) a light source that irradiates the object and is capable of output modulation, (c) am image capture device, (d) the display device, (e) a focusing device located along one of the optical paths, (f) at least one stage coupled to at least one component for controlling one or more of a position and an orientation of the component, (g) an electronically controlled aperture located along one of the optical paths, and (h) an electronically controlled filter located along at least one of the optical paths; (19) the composite optical images are provided during a procedure selected from the group consisting of (a) a medical procedure, (b) a medical ophthalmic procedure, (c) an ophthalmic intraocular lens replacement procedure, (d) an ophthalmic phacoemulsification procedure, (e) a medical restorative procedure, (f) a medical therapeutic procedure, (g) a medical diagnostic procedure, (h) a medical preventative procedure, (i) a medical research procedure, (j) a manufacturing inspection procedure, (k) a manufacturing assembly procedure, and (l) a research or engineering visualization or demonstration procedure; or (20) the object or source includes an object selected from the group consisting of (a) human tissue, (b) a human organ, (c) a human eye, (d) a rigid object, (e) a deformable object, (f) an expandable or contractible object and (g) an animate object, (h) an inanimate object; (21) the second component optical images include one or more images selected from the group consisting of (a) captured physical object images, (b) magnetic resonance images, (c) coherence tomography image(s), (d) optical coherence tomography images, (e) a computer generated polygonal graphic representation of an object, (f) an image that is in a format that can be manipulated by a graphical animation program, (g) an image that is in a format the can be manipulated by a graphical 3-D CAD program.

Numerous further variations of the first aspect of the invention are possible and may, for example, include combinations of the above noted variations.

A second aspect of the invention provides a system for providing composite optical images to an eye or eyes of an observer wherein the composite optical images are included of first component optical images of an object along with second component optical images that are to be displayed in relationship to the first component optical images, the system including: (a) a beam splitter; (b) means for directing the first component optical images along a first optical path to a first beam splitter and from the beam splitter along second and third optical paths to a composite optical image viewing location and to an image capture device, respectively, wherein the image capture device provides first electronic data corresponding to the first component optical images; (c) means for using the first electronic data to provide second electronic data corresponding to second component optical images to be viewed along with the first component optical images and providing said second electronic data to an electronic image display device to provide said second component optical images; (d) means for directing the second component optical images along a fourth optical path to a second beam splitter and then along a fifth optical path to the composite optical image viewing location such that the first component optical images and the second component optical images are overlaid to provide said composite optical images.

Numerous variations of the second aspect of the invention are possible and include, for example: (1) the second beam splitter being the same as the first beam splitter and the second and fifth optical paths being the same optical path; (2) a sixth optical path extending from the second beam splitter to a second optical image capture device and wherein captured second component optical image information provides at least a portion of the other data and is analyzed in combination with the first electronic data to produce said second electronic data; (3) the second image capture device being the same as the first image capture device; (4) the first component optical images includes optical images selected from the group consisting of (a) physical optical images, (b) electronic optical images, (c) emission optical images, and (d) hybrid optical images; (5) the second beam splitter is different from the first beam splitter; (6) a third beam splitter that is different from both the first and second beam splitters and which is located along the fourth optical path and which splits the fourth optical path into one branch that continues to the second beam splitter and one branch that directs the second component optical image onto a second image capture device which in turn provides at least portion of the other data and is analyzed in combination with the first electronic data to produce said second electronic data; (7) the first component optical images include physical optical images and wherein the system additionally includes a light source for directing light into an object positioning region that is located at the beginning of the first optical path; (8) the first component optical images include physical optical images and wherein the system additionally includes a light source for directing light into an object positioning region that is located at the beginning of the first optical path wherein the light source provides light selected from the group consisting of (a) visible light, (b) UV light, and (c) IR light; (9) the first component optical images include physical optical images and wherein the system additionally includes a light source for directing light into an object positioning region that is located at the beginning of the first optical path, and providing one or more optical components between the light source and the object positioning region wherein at least one of the one or more optical components is selected from the group consisting, of (a) a lens, (b) a mirror, (c) a mechanical or electronic shutter, (d) a prism, (e) a diffraction grating, (f) a filter; (10) providing one or more optical components located along one or more of the first -fifth fifth optical paths wherein the one or more optical components includes at least one component selected from the group consisting of: (a) a lens, (b) a mirror, (c) a shutter, (d) a prism, (e) a diffraction grating, and (f) a filter; (11) images reaching the beam splitter via the first and fourth optical paths being provided in time modulated forms such that images reaching the image capture device along the third optical path at selected times are the images carried along the first optical path but not the fourth optical path while at other times the images reaching the image capture device are the images carried along the fourth optical path but not the first optical path; (12) the images represented by the data provided along the second electronic path and displayed by the electronic image display device do not, include images provided along the first optical path; (13) the using of the first electronic data includes determining positioning information that places the second component optical images and the first component optical images within a desired tolerance by calculating a display position for the second component optical images based, least in part, on captured positions of the first component optical images, and wherein the calculation optionally includes spatial comparisons of prior captured first component optical images and prior captured second component optical images; (14) means for adjusting an optical path by adjusting at least one component of the of system, wherein the component is selected from the group consisting of (a) at least one beam splitter, (b) the display device, (c) the image capture device, (d) a positioning of the object, (e) an image focusing component located along one of the optical paths, (f) a filter located along one of the optical paths, (g) a shutter located along one of the optical paths, (h) an aperture along one of the optical paths, and (i) a mirror located along one of the optical paths; (15) means for adjusting an optical path by adjusting at least one component of the of system wherein the means for adjusting provides for adjusting in a manner and at a time selected from a group consisting of (a) manually during operation, (b) manually during calibration, (c) partially automatically during operation, (d) partially automatically during calibration, (e) automatically during operation, and (f) automatically during calibration; (16) means for adjusting an optical path by adjusting at least one component of the of system wherein the means for adjusting provides for automatic adjustment via, at least in part, feedback provided by second component optical images captured by the second image capture device; (17) the means for using includes processing the first electronic data using a programmed computer that is also programmed to control one or more system components and wherein at least one of the one more system components are selected from: (a) an electronic shutter located along one of the optical paths, (b) modulation of a light source that irradiates the object, (c) the image capture device, (d) the display device, (e) a focusing device located along one of the optical paths, (f) at least one stage coupled to at least one component for controlling one or more of a position and orientation of the component, (g) an electronically controlled aperture located along one of the optical paths, and (h) an electronically controlled filter located along at least one of the optical paths; (18) the composite optical images are provided during a procedure selected from the group consisting of (a) a medical procedure, (b) a medical ophthalmic procedure, (c) an ophthalmic intraocular lens replacement procedure, (d) an ophthalmic phacoemulsification procedure, (e) a medical restorative procedure, (f) a medical therapeutic procedure, (g) a medical diagnostic procedure, (h) a medical preventative procedure, (0 a medical research procedure, (j) a manufacturing inspection procedure, (k) a manufacturing assembly procedure, and (I) a research or engineering visualization or demonstration procedure; (19) the source or object includes an object selected from the group consisting of (a) human tissue, (b) a human organ, (c) a human eye, (d) a rigid object, (e) a deformable object, (f) an expandable or contractible object and (g) an animate object, (h) an inanimate object; (19) the second component optical images include one or more images selected from the group consisting of (a) captured physical object images, (b) magnetic resonance images, (c) coherence tomography image(s), (d) optical coherence tomography images, (e) a computer generated polygonal graphic representation of an object, (f) an image that is in a format that can be manipulated by a graphical animation program, (g) an image that is in a format the can be manipulated by a graphical 3-D CAD program.

Numerous further variations of the second aspect of the invention are possible and may, for example, include combinations of the above noted variations.

A third aspect of the invention provides a method of providing composite optical images to an eye or eyes (91) of an observer wherein the composite optical images are included of first component optical images of a source or object (81) along with second component optical images that are to be displayed in relationship to the first component optical images, the method including: (a) providing the source or object that is to provide the first component optical image; (b) providing a beam splitter (111); (b) providing an electronic image display device (141); (c) providing an image capture device (121); (d) providing a data processing device (131); (e) directing light from the source of object along a first optical path (101) extending from an object to the beam splitter and then from the beam splitter along a second optical path (102) to the eye or eyes of an observer and along a third optical path (103) to the image capture device, wherein the image capture device creates first electronic image data; (f) using, at least in part, the first electronic image data and additional information to produce second electronic image data corresponding to a second component optical image and supplying said second electronic image data to the electronic image display device; (g) directing light from the electronic image display device along a fourth optical path (104) to the beam splitter and from the beam splitter along the second and third optical paths to the eye or eyes of the observer and to the image capture device such that a composite optical image is presented to the eye or eyes of the observer.

A fourth aspect of the invention provides a system for providing composite optical images to an eye or eyes (91) of an observer wherein the composite optical images are included of first component optical images of an a source or object (81) along with second component optical images that are to be displayed in relationship to the first component optical images, the system including: (a) a beam splitter (111); (b) an electronic image display device (141); (c) an image capture device (121); (d) a data processing device (131); (e) a first optical path (101) extending from a source or object positioning location to the beam splitter; (f) a second optical path (102) extending from the beam splitter to a composite optical image viewing location; (g) a third optical path (103) extending from the beam splitter to an input of the image capture device; (h) a first electronic signal path (151) connecting the output of the image capture device to a data processing device; (i) a second electronic signal path (152) connecting the output of the data processing computer to an input of the electronic image display device; and (j) a fourth optical path (104) extending from an output of the electronic image display device to the beam splitter, wherein the first optical path transmits an optical image from the source or object positioning location to the beam splitter and from the beam splitter along both the second and third optical paths, wherein, based on one or more parameters associated with an image received by the image capture device, and transmitted along the first electronic path, the data processing device provides data along the second electronic path wherein the data represents images to be displayed by the electronic image display device, wherein the fourth optical path transmits the second component optical images from the electronic image display device to the beam splitter where after the images are split and travel along the second and third optical paths, and wherein the second component optical images and the first component optical images are overlaid along both the second and third optical paths such that the second optical path provides the composite optical image to the viewing location while the third optical path provides both the second component optical image and first component optical image to the image capture device.

A fifth aspect of the invention provides a method of providing composite optical images to an eye or eyes (91) of an observer wherein the composite optical images are included of first component optical images of a source or object (81) along with second component optical images that are to be displayed in relationship to the first component optical images, the method including: (a) providing the object (81) that is to provide the first component optical images; (b) providing a first beam splitter (211-1) and a second beam splitter (211-2); (c) providing an electronic image display device (241); (d) providing an image capture device (221); (e) providing a data processing device (231); (f) directing light from the object along a first optical path (201) extending from a source or object to the first beam splitter and then from the first beam splitter along both a second optical path (202) and a third optical path (203), wherein the third optical path leads to the image capture device which creates first image data while the second optical path leads to the second beam splitter (211-2) and from there along a fifth optical path (205) to the eye or eyes of an observer (203); (g) using, at least in part, the first image data and additional information to produce second image data corresponding to second component optical images and supplying said second image data to the electronic image display device; (h) directing light from the electronic image display device along a fourth optical path (204) to the beam splitter and from the beam splitter along the fifth optical path (205) to the eye or eyes of the observer.

A sixth aspect of the invention provides a system for providing composite optical images to an eye or eyes (91) of an observer wherein the composite optical images are included of first component optical images of a source or object (81) along with second component optical images that re to be displayed in relationship to the first component optical images, the system including: (a) a first beam splitter (211-1); (b) a second beam splitter (211-2); (c) an electronic image display device (241); (d) an image capture device (221); (e) a data processing device (231); (f) a first optical path (201) extending from an object position location to a the first beam splitter; (g) a second optical path (202) extending from the first beam splitter to the second beam splitter and a third optical path (203) extending from the first beam splitter to the image capture device; (h) a first electronic data path (251-1) extending from the image capture device to the data processing device and a second electronic data path (251-2) extending from the data processing device to an electronic image display device; (i) a fourth optical path extending from the electronic image display device to the second beam splitter; (j) a fifth optical path extending from the second beam splitter to -a composite optical image viewing location wherein the fifth optical path carries images from the second and forth optical paths to said composite optical image viewing location, wherein the data processing device provides second electronic image data for display by said display device wherein the second electronic image data is derived at least in part using data generated by the image capture device.

A seventh aspect of the invention provides a method of providing composite optical images to an eye or eyes (91) of an observer wherein the composite optical images are included of first component optical images of a source or object (81) along with second component optical images that are to be displayed in relationship to the first component optical images, the method including: (a) providing the source or object (81) that is to provide the first component optical images; (b) providing a first beam splitter (311-1) and a second beam splitter (311-2); (c) providing an electronic image display device (341); (d) providing an image capture device (321); (e) providing a data processing device (331); (f) directing light from the source or object along a first optical path (301) extending from the object to the first beam splitter and then from the first beam splitter along a second optical path (302) to the second beam splitter (211-2) and then along both a fifth optical path (305) to the eye or eyes of an observer and along a third optical path (303) to the image capture device, wherein the image capture device creates first image data; (g) using, at least in part, the first image data and additional information to produce second image data corresponding to second component optical images and supplying said second image data to the electronic image display device; (h) directing light, in the form of the second component optical image, from the electronic image display device along a fourth optical path (204) to the first beam splitter and from the first beam splitter along the second, fifth, and third optical paths, wherein the fifth optical path provides a composite optical image of the second component optical images and the first component optical images to the eye or eyes of the observer and the third optical path provides the second component optical images to the image capture device and wherein data obtained from the image capture device from at least a portion of the second component optical images provides at least a portion of the additional information.

An eight aspect of the invention provides a system for providing composite optical images to an eye or eyes (91) of an observer wherein the composite optical images are included of first component optical images of a source or object (81) along with second component optical images that are to be displayed in relationship to the first component optical images, the system including; (a) a first beam splitter (311-1); (b) a second beam splitter (311-2); (c) an electronic image, display device (341); (d) an image capture device (321); (e) a data processing device (331); (f) a first optical path (301) extending from an object position location to the first beam splitter; (g) a second optical path (302) extending from the first beam splitter to the second beam splitter; (h) a fifth optical path (305) and a third optical path (303) extending from the second beam splitter to a viewing location and to an image capture device respectively; (i) a first electronic data path (351-1) extending from the image capture device to the data processing device and a second electronic data path (251-2) extending from the data processing device to an electronic image display device; (j) a fourth optical path extending from the electronic image display device to the first beam splitter; wherein the second, fifth, and third optical paths carry both the first component optical images and the second component optical images such that composite optical images are presented at the viewing location; and wherein the data processing device provides second electronic image data for display by said electronic image display device wherein the second electronic data is derived at least in part using data generated by the image capture device.

A ninth aspect of the invention provides a method of providing composite optical images to an eye or eyes (91) of an observer wherein the composite optical images are included of first component optical images of a source or object (81) along with second component optical images that are to be displayed in relationship to the first component optical images, the method including: (a) providing a source or object (81) that is to provide first component optical images; (b) providing a first beam splitter (411-1), a second beam splitter (411-2), and a third beam splitter (411-3); (c) providing an electronic image display device (441); (d) providing a first image capture device (421-1) and a second image capture device (421-2); (e) providing a data processing device (431); (f) directing light from the source or object along a first optical path (401) extending from the object to the first beam splitter and then along a second optical path (402) and a third optical path (403) wherein the second optical path extends from the first beam splitter to the second beam splitter while the third optical path extends from the first beam splitter to the first image capture device; (g) directing light reaching the second beam splitter from the second optical path along a fifth optical path (405); (h) converting images received by the first image capture device into first image data and using, at least in part, the first image data and additional information to produce second image data corresponding to second component optical images and supplying said second image data to the electronic image display device; (i) directing light from the electronic image display device along a fourth optical path (404) to the third beam splitter and from there along both a sixth and a seventh optical path, wherein the sixth optical path leads to the second beam splitter and then to the fifth optical path, wherein the second component optical images and the first component optical images form composite optical images that are presented to the eye or eyes of an observer, while the seventh optical path extends from the third beam splitter to a second image capture device which provides electronic image data to the data processing device which is at least in part used as a portion of the additional information.

A tenth aspect of the invention provides a system for providing composite optical images to an eye or the eyes (91) of an observer wherein the composite optical images are included of first component optical images of a source or object (81) along with second component optical images that are to be displayed in relationship to the first component optical images, the system including: (a) a first beam splitter (411-1); (b) a second beam splitter (411-2); (c) a third beam splitter (411-3); (d) an electronic image display device (441); (e) an first image capture device (421-1); (f) a second image capture device (421-2); (g) a data processing device (431); (h) a first optical path (201) extending from an object position location to the first beam splitter; (i) a second optical path (202) extending from the first beam splitter to the second beam splitter and a third optical path (203) extending from the first beam splitter to the first image capture device; (j) a first electronic data path (251-1) extending from the image capture device to the data processing device and a second electronic data path (251-2) extending from the data processing device to an electronic image display device; (k) a fourth optical path extending from the electronic image display device to the third beam splitter; (l) a sixth and seventh optical path extending from the third beam splitter to the second beam splitter and the second image capture device, respectively; (m) a fifth optical path extending from the second beam splitter to a composite optical image viewing location wherein the fifth optical path carries images from the second and forth optical paths to said composite optical image viewing location, wherein the data processing device provides second electronic image data for display by said display device wherein the second electronic data is derived at least in part using data generated by the first and second image capture devices.

Numerous variations to the third-tenth aspects of the invention, are possible and include for example those noted above with regard to the first and second aspects of the invention.

An eleventh aspect of the invention provides a method of providing composite optical images to an eye or eyes of an observer wherein the composite optical images are included of first component optical images of a source or object along with second component optical images that are to be displayed in relationship to the first component optical images, the method including: (a) directing first component optical images from a source or object to a first beam splitter and thereafter directing split first component optical images to a first image capture device located along a first image capture path and to a viewing location located along a first viewing location path; (b) directing second component optical images from an electronic image display device to a second beam splitter and thereafter directing split second component optical images to a viewing location along a second viewing location path having at least a terminal portion that overlays a terminal portion of the first viewing location path; (c) using at a portion of data created from the first component optical image captured by the first image capture device in generating electronic image data that is provided to an electronic image display device to create updated second component optical images.

Numerous variations of the eleventh aspect of the invention are possible and include, for example: (1) the second beam splitter being the same as the first beam splitter; (2) the first component optical images include optical images selected from the group consisting of (a) physical optical images, (b) electronic optical images, (c) emission optical images, and (d) hybrid optical images; (3) the second beam splitter being different from the first beam splitter; (4) the first component optical images include physical optical images and the method additionally includes directing light from a light source onto an object located at the beginning of the first optical path that gives rise to the physical optical images and wherein the light source optionally produces light selected from the group consisting of (a) visible light, (b) UV light, and (c) IR light; and wherein the method optionally includes providing one or more optical components between the light source and the object wherein at least one of the one or more optical components is selected from the group consisting of: (a) a lens, (b) a mirror, (c) a mechanical or electronic shutter, (d) a prism, (e) a diffraction grating, and (f) a filter; and wherein the method optionally providing one or more optical components located along a path traveled by either one or both of the first component optical image and the second component optical image, wherein the one or more optical components includes at least one component selected from the group consisting of: (a) a lens, (b) a mirror, (c) a shutter, (d) a prism, (e) a diffraction grating, and (f) a filter; (5) at least one of the first component optical image or second component optical image reaching the beam splitter are provided in time modulated forms such that images reaching an image capture device at a given times are only first component optical images while at other times are the images reaching an image capture device are only second component optical images; (6) the second component optical images do not include image that are the same as first component optical images.

A twelfth aspect of the invention provides a system for providing composite optical images to an eye or eyes of an observer wherein the composite optical images are included of first component optical images of a source or object along with second component optical images that are to be displayed in relationship to the first component optical images, the method including: (a) means for directing first component optical images from a source or object to a first beam splitter and thereafter directing split first component optical images to a first image capture device located along a first image capture path and to a viewing location located along a first viewing location path; (b) means for directing second component optical images from an electronic image display device to a second beam splitter and thereafter directing split second component optical images to a viewing location along a second viewing location path having at least a terminal portion that overlays a terminal portion of the first viewing location path; (c) means for using at a portion of data created from the first component optical image captured by the first image capture device in generating electronic, image data that is provided to an electronic image display device to create updated second component optical images.

Numerous variations to the twelfth aspect of the invention are possible and include for example those noted above with regard to the eleventh aspect of the invention and those note above with regard to the second aspect of the invention.

Other aspects of the invention will be understood by those of skill in the art upon review of the teachings herein. Other aspects of the invention may involve combinations of the above noted aspects of the invention. These other aspects of the invention may provide various combinations of the aspects presented above as well as provide other configurations, structures, functional relationships, and processes that have not been specifically set forth above.

DETAILED DESCRIPTION OF PREFERRED EMBODIMENTS

Figure 1:
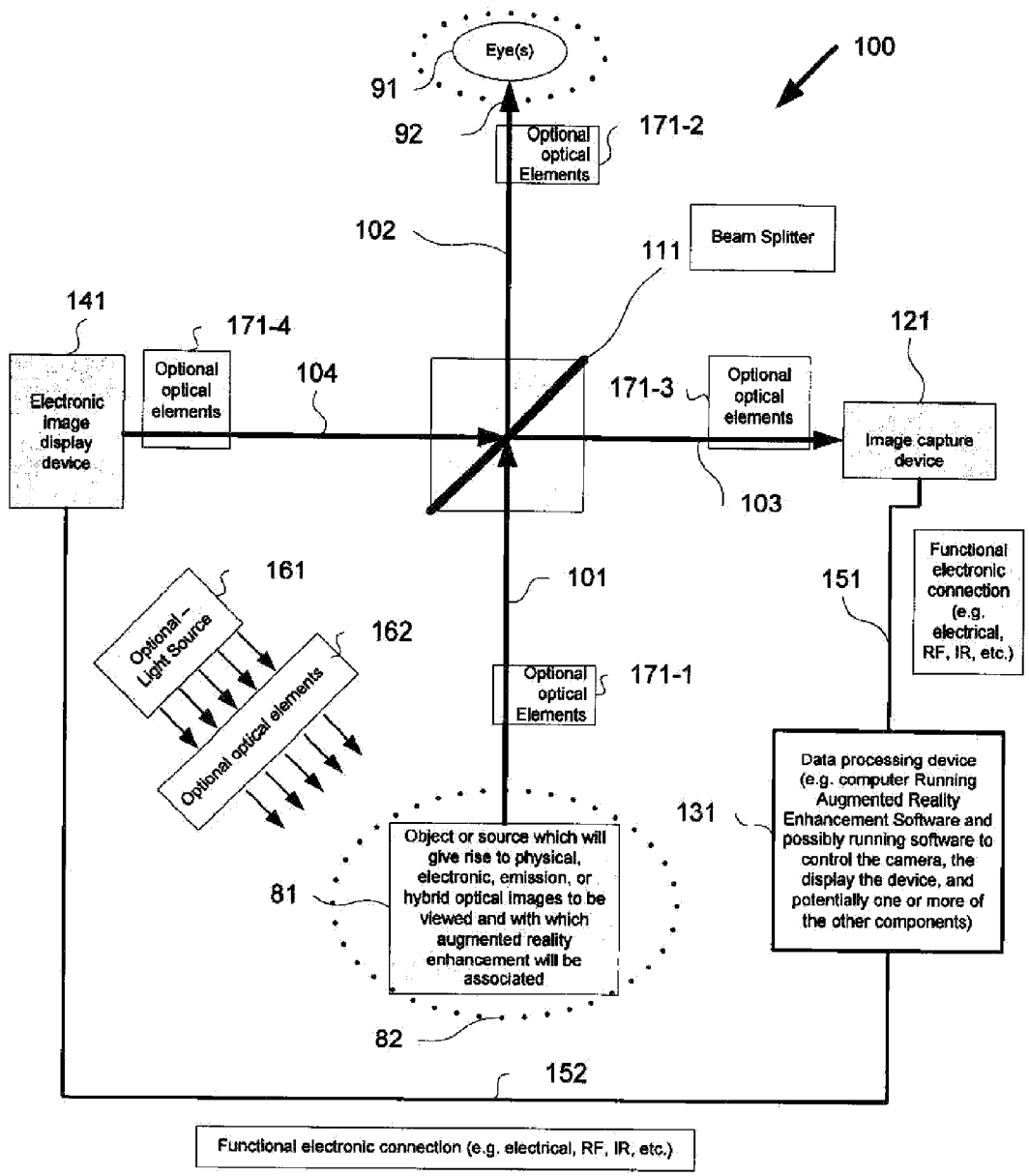
FIG. 1 provides a block diagram showing sample components and sample component relationships according to a system of a first embodiment of the invention wherein the system provides for optical formation of a composite optical image using a single beam splitter to direct a preliminary optical image (e.g. a physical optical image, a first electronic optical image, an emission optical emission, or hybrid image) and an electronic optical image (e.g. a second electronic optical image) along both a viewing optical path and along an image capture optical path.

Defintions:

As used herein an "optical image" is a visual reproduction of an object using an optical system. The optical system may involve light reflected from or transmitted from a source directly to the eye of an observer or it may involve such reflected or transmitted light as modified by an external system of mirrors, lenses, apertures, shutters, and the like (e.g. from reflected, refracted, and/or diffracted light waves). The optical image may originate from a diffuse source of radiation (e.g. a physical object having a microscopically rough surface from which radiation is reflected) or from an electronically controlled radiating or emission source (e.g. an LED, backlit LCD, CRT, or other image producing emission source which is driven by image data that has been electronically transmitted to the display). An optical image produced directly by a diffuse source without an intermediate emission source along the optical path shall be termed a "physical optical image" while an optical image produced by an electronic emission source without an intervening diffuse reflector along the optical path shall be termed an "electronic optical image". An optical image produced by an emission source that is a non-electronic emission source, shall be termed an "emission optical image" An optical image produced by at least two of a diffuse reflective source, and electronic emission source, and a non-electronic emission source, shall be termed a "hybrid optical image".

As used herein an "optical path" is a path along which light waves travel from one position to another and along which the light waves may encounter optical elements that shape or define an image (e.g. size, focal plane, contrast, wavelengths, and the like) or the actual path of travel itself and wherein the optical elements may include, e.g. one or more of lens, mirrors, diffraction gratings, prisms, apertures, filters, shutters, and the like)

As used herein an "electronic image" is an image produced by translation of electronic data into a visual representation wherein the data is created, stored or transmitted in in a form requiring electronic interpretation (e.g. a series of binary voltage, current, magnetic, or even optical pulses) and is transformed into a visual image for perception by the eye using some form of electrical or electronic controlled display device. An electronic image may be a captured image of a physical object (i.e. a diffuse reflector), a captured image from a non-electronic emission source, a captured image from an electronic source, or a captured image from a hybrid emission, or an image created by a computer (e.g. produced by CAD software, computer animation software), or a combination of these.

As used herein a "component optical image" is one of a physical optical image, an emission optical image, an electronic optical image, or a hybrid optical image.

As used herein "composite optical image", "overlaid optical image", and "merged optical image" unless specifically indicated otherwise are substantially synonymous terms that refer to optical images that are created by the spatial optical merging of a at least two component optical images, i.e. first and second optical images wherein the first optical images includes one of a physical optical image, a first electronic optical image, an emission optical image, or a hybrid optical image and wherein the second optical image is a an electronic optical image (e.g. a second electronic optical image). Temporal merging or simultaneity of component optical images of a composite optical image (e.g. the display of both physical optical and electronic optical images simultaneously) may or may not exist. In some embodiments, simultaneous and even continuous display of both the first and second optical images may exist while in other embodiments, the first and second images will alternatively be turned on and off along their respective optical paths to provide a perceived temporal merging of the images to the eye(s) of a viewer but temporally separated images to an image capture device.

As used herein a "electronic display device" or an "electronic image display device" is any device that converts electronic data (e.g. digital data) into an optical image that may be viewed directly or indirectly by the eye of an observer or that may be transmitted along a desired optical path, The display device may be of a digital form (e.g. LED display, LCD display) or analog form (e.g. CRT display).

As used herein an "image capture device" is a device that captures the spatial configuration of an image and translates that the image into data that may include not only spatial information but color, intensity, and temporal information. The captured image may be supplied to a display device directly or not at all and/or it may be supplied to a data processing device such as a digital signal processor or a programmed computer for analysis or manipulation. An image capture device may take a variety of forms such as, for example, a digital camera, a digital video camera, a CCD array, a photocell over which light is scanned or which is translated to sequentially read different portions of an image. Such devices may be configured to capture macro-scale images or microscopic images.

As used herein "an electronic path" is a functional connection over which electronic signals are passed from one electronic device to another. The electronic path may take the form of a current carrying wire or electromagnetic signal that begins at one device and is received by a second device at the end of the electronic path. The electronic path may include, numerous electronic components that shape, strengthen, or other manipulate an electronic signal as it move from the first electronic device to the second electronic device.

As used herein "beam splitter" is intended to be a generic term covering various optical elements and optical element combinations that can be used to (1) split a beam or an optical image so that the split beam or optical image travels along at least two different paths and (2) combine the two appropriately presented beams or images such that the combined beams or images (i.e. composite optical images) travel along one or more common paths. A beam splitter, for example, may be formed from a partially silvered mirror that is located appropriately relative to an incoming optical path (e.g. at 45 degrees to the incoming path), by multiple partially silvered mirrors, by a cube or other geometric shape formed from two or more triangular prisms. Beam splitter technology is well known in the art and is described in, for example, U.S. Pat. No. 7,701,583.

Embodiments in General:

The present disclosure sets forth four primary, specific, and exemplary system embodiments of the invention. Each of these primary embodiments involves the viewing of a composite optical image formed by at least two distinct component optical images (a first component optical image that is one of a physical optical image, an electronic optical image, an emission optical image or a hybrid optical image) and a second component optical image that is an electronic optical image that is presented in relationship to the first component optical image to provide an enhanced or augmented visual representation associated with the first component optical image. In some of these embodiments, the first component optical image is a physical optical image while the second component optical is an electronic optical image. In other embodiments the first component optical image is an electronic optical image while the second component optical image is also an electronic optical image. The first embodiment requires at least one beam splitter, the second and third embodiments require at least two beam splitters, while the fourth requires at least three beam splitters. Each embodiment also requires at least one or two image capture devices, at least one data processing device, and at least one electronic display device. Variations of each embodiment may add in additional electronic components, optical components, and mechanical components as well as a variety of different hardwired or programmed control and monitoring elements to allow real time feedback and enhancement of system performance and/or information logging.

As will be discussed in further detail below, embodiments of the present invention are based, in part, upon the use of an optical path splitting/merging arrangement (i.e. using at least one beam splitter) to provide splitting of individual component optical images (e.g. into viewing and capture paths) while providing a viewing path along which a composite optical image is presented and possibly providing a composite optical image path for image capture purposes as well The systems and methods of the various embodiments of the invention also include, in addition to at least one beam splitter, at least one image capture device, at least one electronic image display device, and at least one data processing device. Embodiments, as appropriate, may also include lighting sources for illuminating physical objects to be viewed and various optical elements for guiding and controlling images as they propagate through the system, These lighting sources may provide, for example, visible, IR, or UV lighting and the resulting images may be physical optical images, emission optical images, or hybrid optical images. Captured images may be used to provide alignment or overlay feedback that can be used in providing improved image merging and thus improved augmentation.

The issued US patents, patent applications, published foreign applications, and other published references that are cited herein are hereby incorporated by reference in their entirety to the same extent as if each was specifically and individually indicated to be incorporated by reference The various exemplary systems and methods set forth herein utilize augmented reality algorithms to, generate electronic optical images and thus composite optical images. Some embodiments of the invention provide real-time electronic optical image feedback relative to physical optical images this feedback can be used to provide real-time calibration of the system and improved presentation of composite optical images. This feedback may be used to improve subsequent image presentation in a reactive manner and/or in a predictive manner.

Image capture devices, or "image capture means", appropriate for the various embodiments of the presentation invention can take on a variety of forms. Examples of such image capture devices include photocell arrays, cameras (e.g. digital cameras or camcorders), charged-coupled devices (CCD), and CMOS Cameras. In such embodiments, the frame rate of the image capture device and of an electronic image display device may be synchronized to allow for the imaging device to view either only a single component optical image, subset of component optical images, or all component optical images as a composite optical image.

As noted above, in some embodiments of the invention the image capture device may capture images at a particular frame and the electronic image display device may display images at a particular frame rate. For example the image capture device may detect images at a frame rate of 30-1000 frames per second (FPS) and in particular embodiments the frame rate may be selected to be between desired narrow band, e.g. between 30-100 FPS, between 100-200 FPS, and the like.

Electronic image display devices, or electronic image display means, appropriate for the various embodiments of the invention can take on a variety of forms. Examples of such devices, or means, include backlit liquid crystal (LCD) displays, plasma displays, cathode ray tubes (CRTs), digital light projectors (DLPs), light emitting diodes (LEDs), and Transparent Organic Light Emitting Diodes (OLEDs).

In different embodiments, the image capture device may view a first component optical image (e.g. physical optical image) alone. a second component optical image (e.g. an electronic optical image alone), a plurality of component optical images but less than all optical images (e.g. two out of three, three out of four, two out of four, and the like) or a composite optical image. Capturing of a first component optical image (e.g. physical optical image) alone may occur by actively transmitting the first component optical image along its optical image path while blocking a second component optical image, arranged to travel on a different optical path from the first component optical image, from reaching a beam, splitter that would result in merging and then transmission to the image capture device. This may be done, for example, by synchronizing the triggering of the frame capture rate of the image capture device and frame emission from the electronic imaging device with an appropriate phase difference. Alternatively this, may be accomplished by shuttering the second component optical image from reaching the beam splitter while the image capture device is to capture the first component optical image (e.g. physical optical image) (e.g. using an acousto-optic modulator or other fast shuttering device). Capturing the second optical image (e.g. an electronic optical image or second electronic optical image) alone may be achieved by shuttering the first component path (e.g. the physical optical image path) or by turning off or shuttering illuminating light from reaching a source of the first image while the image capture device is capturing the second component optical image. If the electronic image display device provides short display pulses, it may be necessary to trigger the display device emission with acquisition triggering of the image capture device (e.g. have them operate in phase with one another). When images from both the paths are allowed, or made, to exist simultaneously, direct capture of composite optical images is possible.

Various embodiments of the invention may make use of optical components at a composite optical image viewing location to allow one or more observers or operators to view the composite optical image. Examples of such optical components include microscopes, ocular indirect virectomy lens, ocular Landers wide angle surgical viewing system. In some embodiment variations, the composite optical image may be projected on to a display screen as opposed to directly entering the observer's eye or eyes.

In some embodiments or embodiment variations as will be discussed hereafter, the composite optical image resulting from the overlaying of a first component optical image (e.g. physical object image) and a second component optical image (i.e. an electronic optical image) may or may not be initially spatially correlated but will become so quickly with successive image presentations as differences in position of overlaid component optical images are ascertained and used to provide feedback control to the configuration of, positioning of and/or orientation of system components and/or display position of the second component optical image on the electronic image display device.

In some embodiments of the invention the data processing device(s) use a technique called markerless tracking to track the second component optical image (e.g. a first or second electronic optical image) relative to the first component optical image (e.g. physical optical image or a first electronic component optical image) and by comparing the positions of the second component optical image relative to known desired positions of second component optical image features relative to actual first component optical image features, one or more corrections can be identified and implemented and thereafter additional images captured, additional processing done, and additional corrections made as necessary to bring and keep the relative positions of the component optical images in appropriate positions. These processes may or may not incorporate predictive techniques (based on past errors in positioning) and/or iterative techniques to yield better and faster merging of the images within desired tolerances.

In some embodiments, involving certain first component optical images (e.g. physical optical images) and certain second component optical images (i.e. electronic optical images), it may be possible that the second component optical images are not a good candidate for markerless tracking. In such instances, fiduciary marks may be introduced into the second component optical image to overcome this limitation. As used herein, "fiduciary marks" are objects inserted into an image and used as a point of reference. The fiduciary marker is either placed into or on an image. Fiduciary marks could be parts of the actual overlay or added. Those marks could be tracked using algorithms such as Scale Invariant Feature Transform (SIFT) or Kanade-Lucas-Tomasi (KLT) feature trackers. Another method would be to directly compare known feature correspondences between the first component optical images and the second component optical images to compute misalignment amounts or correction factors.

In addition to the possibility of ensuring alignment and orientation of the first and second component optical images (and any additional component optical images) via feedback, another job for the data processing device or devices (e.g. computer or computers) may be to manipulate existing electronic optical images (e.g. position, orient, scale, color data associated with such images) or to create and manipulate electronic optical images using augmented reality algorithms which are well known in the field. Examples of such algorithms are described in (1) Kato, H., Billinghurst, M. "Marker tracking and hmd calibration for a video-based augmented reality conferencing system"; (2) In Proceedings of the 2nd IEEE and ACM International Workshop on Augmented Reality (IWAR 99), October 1999; (3) R. Azuma, A Survey of Augmented Reality Presence: Teleoperators and Virtual Environments, pp. 355-385, August 1997; and (4) P. Milgram and A. F. Kishino, Taxonomy of Mixed Reality Visual Displays IEICE Transactions on Information and Systems, E77-D(12), pp. 1321-1329, 1994.

In some embodiments of the invention, a combination of markless tracking (to ascertain first and second component optical image positions and/or orientations) and augmented reality algorithms are used to yield data for a next electronic optical image to be displayed. Markerless tracking algorithms are known in the art and are described for example, in (1) L. Vacchetti, V. et al. *IEEE Transactions on Pattern Analysis and Machine Intelligence*, 26 (10): 1385-1391,2004; (2) L. Vacchetti et al. "Combining Edge and Texture Information for Real-Time Accurate 3D Camera Tracking," International Symposium on Mixed and Augmented Reality, Arlington, Va., November 2004; (3) L. Vacchetti, V. et al. "Stable 3-D Tracking in Real-Time Using Integrated Context Information," Conference on Computer Vision and Pattern Recognition, Madison, Wisc., June 2003; (4) V. Lepetit at al. "Fully Automated and Stable Registration for Augmented Reality Applications," International Symposium on Mixed and Augmented Reality, Tokyo, Japan, 2003.

Some embodiments of the invention and variations thereof, use programmed algorithms or logic for aligning component optical images and to render (i.e. convert from graphic data to visual form) or even create electronic optical images for presentation to the electronic image display device while other embodiment may limit such programmed algorithms to only the rendering and creation activities.

In some embodiments, an ideal augmented reality image (e.g. an image that consists of a physical optical image component and an electronic optical image component) may be created within the computer and it may be used for comparison to captured composite optical images to determine if a composite optical image has been properly created and/or presented. In these embodiments, it may be possible to determine an alignment error in the components of the composite optical image. Correction information can then be calculated and used to adjust the position of the electronic optical image output by electronic image display device, e.g. by use of a Euclidean Transformation. These and other techniques are described in Yi et al. An Invitation to 3-D Vision; Hartley, R.~I. and Zisserman, A. "Multiple View Geometry in Computer Vision", Cambridge tions may be performed by the separate manipulation device. University Press, 2000. In some embodiments, data manipulations may be performed by a data manipulation device that is incorporated into the image capture device while in other embodiments, a portion of the data manipulations may performed by a separate data manipulation device, while in other embodiments, all data manipula In some embodiments, misaligned first component optical images (e.g. physical optical images) and second component optical images (i.e. electronic optical images) may be corrected by the physical movement of or reconfiguration of system components alone, by display/image positioning adjustments, or by a combination. The physical movement of system components may involve, for example, movement of the display device, the image capture device an/or the beam splitter while reconfigurations may involve, for example, opening and closing of apertures (e.g. irises) and setting adjustments for focusing components.

In some embodiments, a single computer source or distributed computing may be used to derive necessary data and/or to control movements and/or operation of system components. Computing capability may exist in the display device and/or in the image capture device.

The correcting of unaligned first component optical images (e.g. physical optical images) and second component optical images (i.e. electronic optical images) by adjustment of the display position on electronic image display device may occur by aligning the second component optical image to the first component optical image using, re-rendering of the electronic optical image based on a mathematic transformation as represented by the following equation:

$$Y=f(U)$$

where U is a vector characterizing the size, location, and orientation of an electronic optical image as shown on the display device. Y is a vector characterizing the size, location, and orientation of the electronic optical image as seen by the image capture device. The mathematical model "f" maps U to Y, where f is a mathematical transformation. Such transformations include linear, affine, homography, nonlinear (strictly speaking homography is nonlinear), look-up tables, and the like.

In augmented reality applications, desired second component optical images, denoted in the following equation as R, are generated to be superimposed with first component optical images, denoted as T, with desired geometrical alignment. The rendering of the electronic optical image R requires the inverse model describing the transformation between the viewing device and the display device:

$$U=f'(R)$$

When the mathematical model of the second component optical image and its inverse do not accurately represent the actual physical system, error occurs such that the second optical image and the first optical image (e.g. electronic optical image and the physical optical image) are not aligned as desired. To ensure accurate alignment between the first component optical images and the second component optical images as seen by the viewing device, the feedback mechanism may capture the rendered composite optical images. The mechanism may then compare the ideal composite optical image and the captured composite optical image and calculates the geometrical alignment error. The geometrical alignment error is the vector (3-D displacement and orientation and image size as characterized by appropriate camera image projection model) between the ideal composite optical image and the measured composite optical image. This error can be mathematically represented as follows:

$$E(k)=R-Y(k),$$

where R is the desired second component optical image rendering vector, which will align with the first component optical image T in a desirable manner determined by the augmented reality software. Y(k) is the measured electronic optical image with iteration index number k. The error vector E(k) is used to make correction for the composite optical image rendering in the following iterative feedback correction:

$$U(k+1)=U(k)+g(E(k))$$

where U(k) is the present rendering vector of the composite optical image, U(k+1) is the next feedback compensated rendering vector of the composite optical image. The function g is ideally the inverse function f'. When the inverse model is not readily available, g can be a gain matrix that is tuned to assure that the error E(k) diminishes to acceptable level over a number of iterations.

In some embodiments, the alignment of the composite optical image is adjusted by adjusting the rendering of the second component optical image onto the electronic image display device. As an example, adjustment of the rendering of the second component optical image can be accomplished using the following methodology. First the viewpoint from which a 3-D model of the second component optical image is to be displayed is computed. Then, from the computed viewpoint, the surface of the 3D model is projected onto the image plane of the electronic image display device using an appropriate virtual camera model (e.g. pinhole). It is also possible to add further rendering steps by distorting the projected 3-D model using a mathematic transformation directly on the pixels. (linear, affine, nonlinear, homography).

The following is an illustrative example of feedback. Let U represent the position and orientation of a 3-D structure represented by the second component optical image in the coordinates of the electronic image display device. The second component optical image is then rendered on the electronic image display device using a projective model as, $$u=\Pi_d q_d(U)$$

where $\Pi_d$ is the virtual display projection, $q_d(U)$ is a Euclidean Transformation (rigid body motion) and u is the second component optical image on the display. The rendered overlay on the display is then captured by the image capture device by another projective transformation $$Y=\Pi_c q_c(u)$$

where $\Pi_c$ is the image capture device projection, $q_c(U)$ is a Euclidean Transformation and y is the image of the second component optical image. Let R represent the desired location of the second component optical image in the image capture device coordinates such that it is overlaid correctly with the first component optical image. R is computed using the location of the first component optical image in coordinates of the image capture device as obtained via markerless tracking. The second component optical image can also be tracked and its virtual location in the camera coordinates can be computed as Y. The feedback update law, U(k+1)=U(k)+g(E(k)) can then be used to adjust U to reduce E to an acceptable level.

First Specific Embodiment:

The first specific embodiment provides an augmented reality system 100 and method allowing an observer to view first component optical images (e.g. physical optical images), that are initially provided on a first optical path, that are combined with second component optical images (e.g. electronic optical images), that are originally provided on a fourth optical path, wherein the overlaying of the two component optical images occurs optically via a beam splitter and wherein branches of the first component optical images and the second component optical images are sent by the beam splitter along a second optical path for viewing by an observer or operator and along a third optical path into an image capture device wherein the captured copies of the first component optical images are used, at least in part, to create or position the second component optical images to be displayed as part of the composite optical image. In some variations of this embodiment, feedback of the relative positions of the captured first component optical images and the captured second component optical images are used to enhance alignment of the images in producing the composite optical image. In some variations of the first embodiment, the creation or transmission of the first component optical images and the second component optical images along the first and fourth optical paths, respectively, are modulated such that at selected times only one of the two component images reaches the image capture device such that capture of individual component images and individual processing of those images can be used to provide enhanced alignment when forming the composite optical images. In some variations of the first embodiment, enhanced alignment occurs manually during a set up procedure, manually during usage, semi-automatically during a set up procedure, semi-automatically during usage, automatically during a set up procedure, or during usage.

The features of and various alternatives to the first embodiment can be better understood by reference to FIG. 1 which provides a block diagram showing sample components and sample component relationships according to a system of a first embodiment of the invention wherein the system provides for optical formation of a composite optical image using a single beam splitter to direct first component optical images and second component optical images along both a viewing optical path (path and along an image capture optical path.

The system of FIG. 1 includes an source or object placement location 82 where the source or object 81 is to be located with a first optical path 101 extending from the source object located within the placement location 82 and a beam splitter 111. First component optical images (e.g. physical optical images) are transmitted along path 101 and are then being split into first and second components which continue along a second optical path 102 and third optical path 103 respectively. The second optical path 102 extends from the beam splitter 111 to a viewing location 92 wherein the eye or eyes 91 of an observer may see the first component optical image of the object or source 81 (when such an object is appropriately located or a source is appropriately activated) while the third optical path 103 extends from the beam splitter to the an image capture device 121 and carries first component optical images, similar to that carried along path 102, to the image capture device. Based on this configuration a first component optical image of an object or source 81 can be simultaneously seen at the end of the second optical path 102 or captured at the end of the third optical path 103. The first component optical image captured by the image capture device 121 can be converted to electronic data and transmitted along electronic path 151 to a data processing device (e.g. to a digital signal processor for hardwired manipulations or to a programmed computer for more readily updatable manipulations) for determination or characterization of selected features (e.g. determination of object orientation, position, and size). This information can in turn be used in preparing data for representation of second component optical images, from an electronic image display device, that is to be displayed in relative position to the first component optical images in a composite optical image that is to be created.

In some embodiment variations, it may be necessary to present second component optical imagers, e.g. electronic optical images, in reversed configurations (e.g. mirror image configurations) relative to first component optical configurations such that when composite optical images reach the eye or eyes of an observer or when they reach the image capture device they will have proper overlaid configurations. Such reversals may be provided via the electronic data and driving of the electronic display device or via optical components located along one or more of the optical paths. Similarly, depending on what purpose may be associated with the composite optical image viewing, it may be desirable to insert additional optical elements to ensure that the viewed composite optical image has a desired orientation relative to the first component optical images that are creating a portion of the composite optical image.

Electronic image data is sent along electronic path 152 to the electronic image display device 141 (e.g. an back lit LCD array, an LED array, a laser or broad area light source whose output can be controllably scanned, filtered, and modulated) whereafter the created electronic optical image (i.e. second component optical image) is transmitted along optical path 104 wherein the image encounters beam splitter 111 at a different angle or face than that of optical path 101 (e.g. the two paths are substantially perpendicular to one another). Upon reaching beam splitter 111 the second component optical image is split into two components, as was the first component optical image, with one branch traveling along second optical path 102 to viewing location 92 and the other traveling along the third optical path 103 to image capture device 121 whereby composite optical images are formed along both optical paths 102 and 103. Of course, depending on the quality of alignment (e.g. size, position, orientation, focus, and even timing) of the first and second component optical images traveling along paths 101 and 104, respectively, the resulting overlap of the composite optical images reaching the viewing location 92 and the image capture device 121 after traveling along paths 102 and 103 may be more or less correlated.

In some variations of the first embodiment of the invention, one or more of the electronic image display device 141, the beam splitter 111, the electronic image capture device 121, and possibly the viewing location 92 and/or the positioning location 82 may be repositionable or reorientable relative to the other components either manually under computer control to help provide improved alignment of composite optical image components (i.e. of the first and second component optical images that hat make up the composite optical images). This repositioning capability may be achieved by placing these components on positioning stages ranging from single to six axis stages. These stages may be manually adjustable or computer controlled (e.g. for control by the data processing computer or by some other controller incorporated into the system).

In some variations of the first embodiment, additional optical elements may be located along one or more of the first-fourth optical paths as indicated by blocks 171-1 to 171-4 in FIG. 1. These optical elements may include apertures, lens, mirrors, filters, shuttering devices (e.g. acousto-optic modulators), additional beam splitters, and the like that may be used to position, size, orient, modulate, split, combine, or vary light wavelengths reaching the viewing or capture positions. Such optical elements may be configurable manually or by computer controlled adjustment.

In some embodiment variations, one or more light sources 161 may be included in the system to direct light onto the object viewing location and in still other embodiments additional optical elements 162 may be included between the light source and the source or object location position. In some such variations, the light source itself may be capable of modulated output while in other embodiments any desired output modulation may be achieved by one or more of the optical elements 162 or 171-1 such that only at selected times do relevant images from optical path 101 actually reach optical paths 102 and 103.

In some embodiments, modulation of the second component optical images occurs by modulating the optical output of the electronic image display device 141 while in other embodiments any necessary modulation is provided by the optical elements 171-4.

In some embodiment variations, the modulation along the first optical path and fourth optical path are coordinated such that only an image from one path or the other reaches that the image capture device at any given time. In still other embodiment variations, some overlap of separate component optical images is allowed to occur but image capture is controlled so that it occurs only when single component optical images are present. In still other embodiment variations no such coordination is provided.

In some embodiments, component optical images may be made, distinguishable by wavelength filtering. In other embodiments, component optical images may be made distinguishable by optically or electronically subtracting a known one of the first component optical or second, component optical images from a composite optical image to yield data providing an approximation of the other of the component optical images. Such captured and extracted component optical image information may be used in enhancing composite optical image creation.

In some preferred embodiment variations, component optical image modulation, image persistence, and refresh rates are set so as to provide the eye of an observer with the appearance of a continuously displayed composite optical image while the image capture device can capture individual component optical images for data manipulation purposes. In other preferred embodiment variations, the first component optical image is presented in such a way so as to provide the appearance of continuity while the second component optical image is presented so as to provide gaps or discontinuities in the image so that a desired distinction between first component optical images and second component optical images may be achieved by the eye or eyes of the observer. In still other preferred alternative implementations a reversed presentation may be provided. in each of these two latter approaches distinct component optical images may or may not be presented to the image capture device.

In some variations of the first embodiment, adequate correlation of images is achieved by manually adjusting positions, alignment, and focusing power of one or more optical components and/or by adjusting an offset parameter or focus plane for the second component optical image as displayed by the electronic image display device. In further variations such manipulations may be performed manually, semi-automatically by electronic or electromechanical devices upon instruction form an observer or system user while in others they may be performed in a fully automated manner by the system itself using computer control in combination with feedback information extracted from successive composite optical images or successive individual component optical images that make up the composite optical images that are captured by the image capture device and then analyzed by the data processing device.

Data storage, capture, analysis, manipulation, and creation performed by the data processing device or devices may take on a variety of forms depending on the details of system usage. For example is the system being used for a particular medical procedure, a manufacturing inspection procedure, is the object that is being viewed rigid or flexible, is the object that is being viewed subject to translational or angular movement during the procedure, is the object that is being viewed subject to changes in shape during the procedure (e.g. subject to resection or ablation, build up by deposition or attachment, expansion or contraction, and the like). Is positioning, size, and orientation of the second component optical image to be determined using only the information associated with captured first component optical image data or is it to include feedback information from captured information associated with the previous second component optical image information as well.

In some embodiment variations the composite optical images may be composed of more than two merged images (e.g. they may be formed from three, four, or even more images) with successive component images (e.g. third, fourth or even more component images) being combined with previously merged but incomplete composite images.

Figure 2:
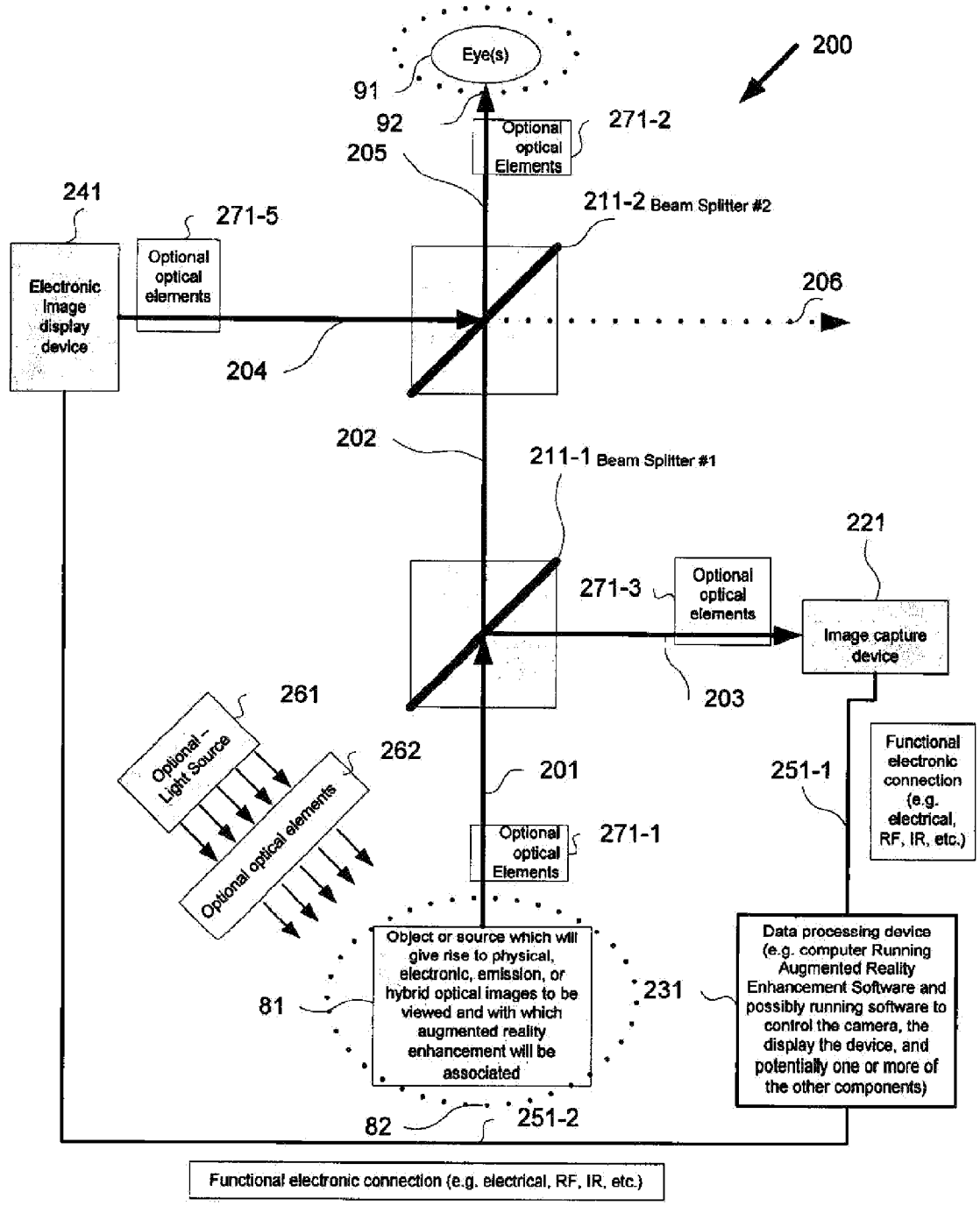
FIG. 2 provides a block diagram showing sample components and sample component relationships according to a system of a second embodiment of the invention wherein the system provides for optical formation of a composite optical image using two beam splitters wherein the first beam splitter directs a branch of a first component optical image (e.g. a physical optical image, a first electronic optical image, an emission optical image, or a hybrid optical image) along an image capture path and the second beam splitter directs both a branch of the first component optical image and a branch of a second component optical image (e.g. second electronic optical image) along a viewing optical path.

Second Specific Embodiment:

The second specific embodiment, as with the first specific embodiment, provides an augmented reality system 200 and method allowing an observer to view a first component optical image (e.g. a physical optical image) that is combined with an a second component optical image (i.e. an electronic optical image). In the second specific embodiment a second beam splitter is used such that only a physical optical image is capable of reaching the image capture device while a composite optical image is capable of reaching the eye or eyes of an observer. The details of an example implementation of this second embodiment can be understood with reference to FIG. 2 wherein like elements are presented with reference numerals similar to those used in FIG. 1 with the exception that the reference numerals have been updated from the 100 series to the 200 series and with other exceptions to be noted below. Due to the presence of the second beam splitter 211-2 the first component optical image is not only directed along the third optical path 203 to the image capture device 221, it moves from the first beam splitter 211-1 to the second beam splitter via the second optical path 202 and then to the eye or eyes of the observer along a fifth optical path 205. The second beam splitter also projects a portion of the image on the second optical path along an unused sixth optical path 206. In this embodiment, the fourth optical path 204 starting with the electronic image display device extends not to the first beam splitter but to the second beam splitter where it is split into path 205 and path 206 branches with the path 205 branch, in combination with the first component optical image forming a composite optical image for presentation to the eye or eyes of an observer.

In this embodiment, as there is no second component optical image presented to the image capture device, such information is not available for feedback usage in providing enhanced overlaying of first and second component optical images and thus complete reliance is given to initial optical set up of the system components and optional system components (e.g. optical components 271-1 to 271-5) and the data analysis and image data generation provided by the data manipulation device. In some variations of this embodiment, the unused composite optical images of the sixth optical path 206 may be presented to the eye or eyes of a second observer, to a display screen, to a second image capture device for image storage, for analysis, and/or for providing some form of system feedback. Many of the alternatives noted above for the first embodiment or set forth in the general discussion may be combined with the features of this embodiment to create further embodiments or embodiment variations. Conversely some of the features of the this embodiment, may be combined with those of the first embodiment or other embodiments presented herein to provide additional system or method enhancements or simplifications (e.g. intentional creation of additional image paths and particularly composite optical image paths allow additional functionality to be obtained, alternatively simplified processing may be implemented by not using feedback with some possible loss in functionality but with faster processing or reduced system complexity and reduced cost)

An advantage of this embodiment over the first embodiment is that temporal image modulation, or other image separation (e.g. possible wavelength separation), methods are not needed to ensure that first component optical image information is available and can be readily recognized and used in creating or relative positioning of second component optical images. Disadvantages of this embodiment involve the inability to use a combination of captured first component optical image data and captured second component optical image data to provide enhanced alignment of the component images making up the composite optical image.

Figure 3:
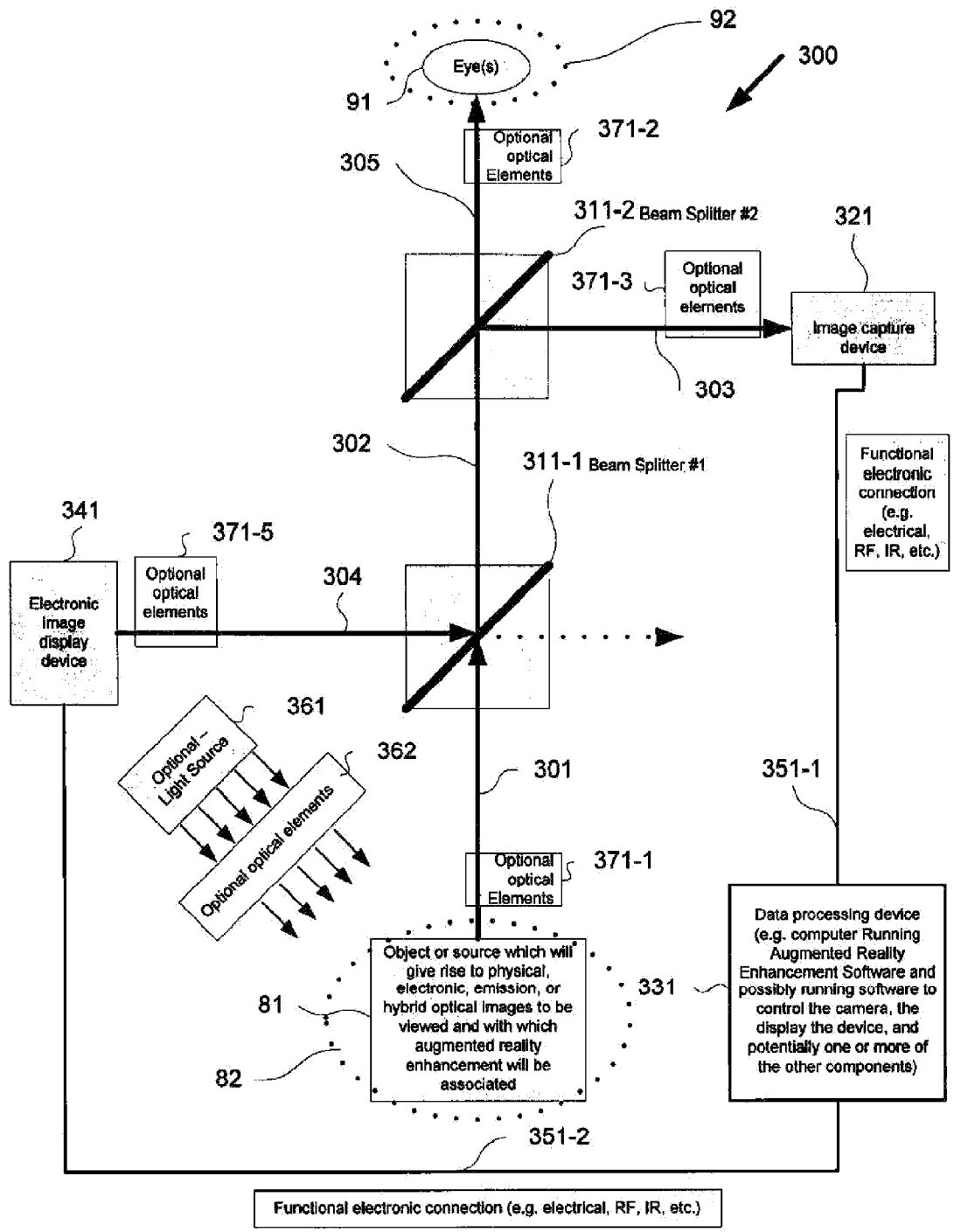
FIG. 3 provides a block diagram showing sample components and sample component relationships according to a system of a third embodiment of the invention wherein the system provides for optical formation of a composite optical image using two beam splitters wherein the first beam splitter merges components of a first component optical image (e.g. a physical optical image, a first electronic optical image, an emission optical image, or a hybrid optical image) and a second component optical image (e.g. a second electronic optical image) along a single optical path that proceeds to the second beam splitter which divides the merged optical images between an image capture path and a composite optical image viewing path.

Third Specific Embodiment:

The third embodiment provides an augmented reality system 300 and method wherein at least two beam splitters are used (e.g. like the second embodiment) with merging of optical paths occurring by perpendicular paths of a first component optical image (optical path 301) and a second component optical image (optical path 304) encountering a first beam splitter 311-1 wherein the merged optical path/composite optical image encounters a second beam splitter 311-2 which divides the path into a viewing portion (optical path 305) and a capture portion (optical path 303). The details of an example implementation of this third embodiment can be understood with reference to FIG. 3 wherein like elements are presented with reference numerals similar to those used in FIGS. 1 and 2 with the exception that the reference numerals have been updated from the 100 or 200 series to the 300 series and with other exceptions to be noted below.

Many of the alternatives noted above for the first and second embodiments or set forth in the general discussion may be combined with the features of this embodiment to create further embodiments or embodiment variations. Conversely the overlaid or composite optical path 302 between the beam splitters 311-1 and 311-2 of the present embodiment may be combined with features of these other embodiments.

A possible advantage of this third embodiment is the creation of an overlapped optical path 302 (between the two beam splitters) that feeds the both the paths leading to image capture 303 and viewing 305 which ensures that the presence of an adequately overlaid composite optical image presented to the image capture device 321 dictates an adequately overlaid composite optical image being presented to the eye or eyes of the observer. A possible disadvantage with this approach relative to the first embodiment is that it involves the need for a second beam splitter which results in an associated loss in optical image intensity.

Figure 4:
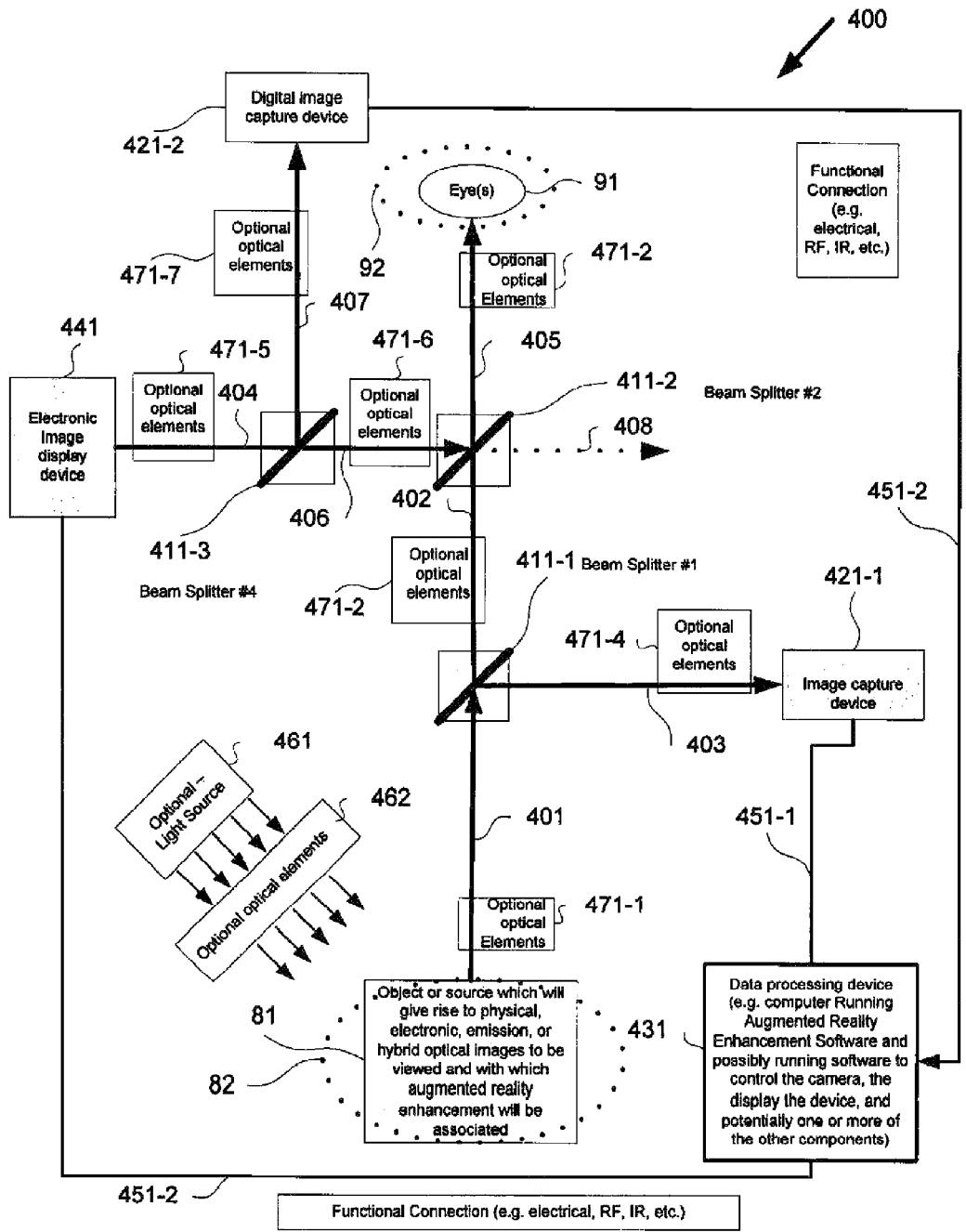
FIG. 4 provides a block diagram showing sample components and sample component relationships according to a system of a fourth embodiment of the invention wherein the system provides for optical formation of a composite optical image using three beam splitters wherein the first beam splitter directs a branch of a first optical image (e.g. a physical optical image, a first electronic optical image, an emission optical image, or a hybrid optical image) along a first image capture path and the second beam splitter directs both a branch of the split first optical image and a branch of a split second component optical image (e.g. a second electronic optical image) as a composite optical image along a viewing optical path and wherein a third beam splitter directs separate branches of the second component optical image (e.g. second electronic optical image) along a second image capture path and to the second beam splitter.

Fourth Specific Embodiment:

The fourth embodiment (as shown in FIG. 4) provides an augmented reality system 400 and method allowing an observer to view a first component optical image (e.g. a physical optical image), originating at the beginning of the first optical path 401, that is combined with a second component optical image (i.e. an electronic optical image), originating at the beginning of the fourth optical path 404, along a fifth optical path and wherein the overlaying of the two component images occurs optically via three beam splitters from path 404 and via two beam splitters from path 401 and wherein copies of the first component optical images and the second component optical images are sent by the first beam splitter 411-1 and a third beam splitter 411-3, respectively, along second and seventh optical paths 402 and 407 into separate image capture devices 421-1 and 422-2. In this embodiment, a sixth optical path connects one branch of the split image from the third beam splitter 411-3 to a second beam splitter 411-2 while the second optical path connects one branch of the split image form the first beam splitter to a another surface of the second beam splitter 411-2. As with the other embodiments presented herein above, optional optical components 471-1 to 471-7 may be located one or more of the first-seventh optical paths. As with the second and third embodiments, features of the fourth embodiment are shown using reference numerals similar to those used for FIG. 1 with the exception that the numerals are now part of the 400 series.

In this embodiment the captured copies of the first component optical images and the second component optical images are used, at least in part, to create, position, and/or align second component optical images to be displayed as part of the composite optical image at position 92. An advantage of this embodiment over certain variations of the first embodiment is that temporal image modulation, or other image separation methods are not needed to ensure that first component optical image information is made available and can be readily recognized for use in creating, positioning or aligning second component optical images with first component optical images since such images are captured by different devices. An advantage over the second, embodiment is that due to the presence of the third beam splitter, and second image capture device, feedback information is available to allow enhanced first component optical image and second component optical image alignment to provide enhanced alignment of the images making up the composite optical images. The advantage over the third embodiment is the same as that compared to the first embodiment.

Many of the alternatives noted above for the first-third embodiments or set forth in the general discussion may be combined with the features of this embodiment to create further embodiments or embodiment variations. Conversely the separate image capture devices of the present embodiment may be worked into variations of these other embodiments.

Further Alternatives:

Numerous other embodiments are possible that may provide embodiments that are distinct form the first four embodiments or may provide enhanced versions of the first to fourth embodiments. Some additional embodiments may provide a different balance of advantages and disadvantages relative to the first four embodiments. For example, embodiments using additional beam splitters are possible, embodiments using a different arrangement of optical paths are possible, embodiments that provide alternative arrangements of viewing paths and image capture paths are possible. Embodiments using various optical path control and adjustment mechanisms are possible. Such adjustment mechanisms may change the relative positions and/or orientations of two or more system components, change the absolute or relative brightness of images traveling along the different optical paths, adjust aperture sizes, filter selected wavelengths, provide temporal, wavelength, and/or intensity modulation of images carried by different optical paths. In different embodiments these adjustments may be made manually, semi-automatically, or automatically during a system calibration process or during normal system use, for example, as part of feedback corrections. Still other alternative embodiments may add in image recording capabilities.

In still other alternative embodiments, electronic images may computer created images, optically created and then electronically captured images, images created by non-light means such as x-rays, CAT scans, NMR scans, ultrasonic scans, or other three-dimensional image generating techniques. Such alternative electronic image generating methods may be provided in a real time manner (e.g. several times per second), in a semi-real-time manner (e.g. several time per minute, one time every several minutes, and the like), or in a static manner. Real time images may be generated from additional image generation source components and image capture components added to the system while static images may be provided from imported previously generated data.

Applications:

Numerous specific applications of the methods and systems set forth here are possible. Two such applications are disclosed in U.S. Provisional Patent Application Nos. 61/358,780 and 61/358,793, each filed Jun. 25, 2010 and entitled "Ophthalmic Surgical Procedures Using Visual Images Overlaid with Visual Representations of Selected Three-Dimensional Data" and "Phacoemulsification Procedures Using Tool Tip to Posterior Capsule Spacing Information Extracted from Real-Time Diagnostic Scan Data", respectively. The first of these applications provides enhanced methods and procedures for placing intra ocular lenses in the eyes of patients while the second provide for an enhanced and more controlled methods and procedures for performing phacoemulsification of the lens of the eyes of patients in preparation for placement of IOLs or in preparation for other procedures. The teachings in these referenced applications are incorporated herein by reference as if set forth in full herein.

Further Comments and Conclusions

Though various portions of this specification have been provided with headers, it is not intended that the headers be used to limit the application of teachings found in one portion of the specification from applying to other portions of the specification. For example, it should be understood that alternatives acknowledged in association with one embodiment, are intended to apply to all embodiments to the extent that the features of the different embodiments make such application, functional and do not otherwise contradict or remove all benefits of the adopted embodiment. Various other embodiments of the present invention exist. Some of these embodiments may be based on a combination of the teachings herein with various teachings incorporated herein by reference.

In view of the teachings herein, many further embodiments, alternatives in design and uses of the embodiments of the instant invention will be apparent to those of skill in the art. As such, it is not intended that the invention be limited to the particular illustrative embodiments, alternatives, and uses described above but instead that it be solely limited by the claims presented hereafter.

We claim:

1. A method of providing composite optical images to an observer wherein the composite optical images are comprised of a first set of component optical images of a source or object along with a second set of component optical images configured to be displayed in relationship to the first set of component optical images, the method comprising:
    directing the first set of component optical images from a source or an object to a first beam splitter and thereafter directing a first split first component of the first set of component optical images to a first image capture viewing location path;
    directing a second set of component optical images from an electronic image display device to a second beam splitter and thereafter directing a second split second component of the second set of component optical images to a viewing location along a second viewing location path having at least a terminal portion that overlays a terminal portion of the first viewing location path;
    using a portion of data created from the first component optical image captured by the first image capture device in generating electronic image data that is provided to an electronic image display device to create an updated second set of component optical images; and
    wherein at least one of the steps of directing further comprises providing the first set of component optical images including physical optical images and directing light from a light source onto an object located at the beginning of the first set of optical path that gives rise to the physical optical images.

2. The method of claim 1, wherein the second beam splitter is the same as the first beam splitter.

3. The method of claim 1, wherein the second beam splitter is different from the first beam splitter.

4. The method of claim 1, wherein the light form the light source comprises at least one of: (1) visible light, (2) UV light, and (3) IR light.

5. The method of claim 4, additionally comprising providing one or more optical components between the light source and the object wherein at least one of the one or more optical components is selected from the group consisting of: (1) a lens, (2) a mirror, (3) a mechanical or electronic shutter, (4) a prism, (5) a diffraction grating, and (6) a filter.

6. The method of claim 5, additionally comprising providing one or more optical components located along a path traveled by either one or both of the first set of component optical images and the second set of component optical images, wherein the one or more optical components include at least one of: (1) a lens, (2) a mirror, (3) a shutter, (4) a prism, (5) a diffraction grating, and (6) a filter.

7. The method of 6, wherein the second set of component optical images do not comprise image that are the same as the first set of component optical images.

8. A method of providing composite optical images to an observer wherein the composite optical images are comprised of a first set of component optical images of an object or source along with a second set of component optical images displayed in relationship to the first set of component optical images, the method comprising:
    directing the first set of component optical images along a first optical path to a first beam splitter;
    directing the first set of component optical images along a second optical path and a third optical path from the first beam splitter to a first image capture device;
    generating a first set of electronic data corresponding to the first set of component optical images captured by the first image capture device and using said first electronic data set in combination with other data to provide a second electronic data set;
    providing the second electronic data set to an electronic image display device to project the second set of component optical images along a fourth optical path onto a second beam splitter; and
    providing a third beam splitter located along the fourth optical path, the fourth optical path being split into one branch that continues to the second beam splitter and one branch that directs the second component optical image onto a second image capture device.

9. A method of providing composite optical surgical images to a physician wherein the composite optical surgical images are comprised of a first set of component optical images of a surgical area along with a second set of component optical images configured to be displayed in relationship to the first set of component optical images, the method comprising:
    directing the first set of component optical images from the surgical area to a first beam splitter and thereafter directing a first split first component of the first set of component optical images to a first image capture viewing location path;
    directing a second set of component optical images from an electronic image display device to a second beam splitter and thereafter directing a second split second component of the second set of component optical images to a viewing location along a second viewing location path having at least a terminal portion that overlays a terminal portion of the first viewing location path; and using a portion of data created from the first component optical image captured by the first image capture device in generating electronic image data that is provided to an electronic image display device to create an updated second set of component optical images.

* * * * *